United States Patent [19]

Lawrence et al.

[11] 4,417,564
[45] Nov. 29, 1983

[54] CENTERING AND WORKING GEMSTONES

[76] Inventors: John C. Lawrence, 50, Heathfield Rd., Acton, London; Andrew D. G. Stewart, The Old Rectory, Ashampstead, Reading, Berkshire; John S. Dodson, 20, Leigh Rd., Cobham, Surrey, all of England

[21] Appl. No.: 269,271

[22] Filed: Jun. 1, 1981

[30] Foreign Application Priority Data

Jun. 4, 1980 [GB] United Kingdom ................ 8018349
Apr. 6, 1981 [GB] United Kingdom ................ 8110751

[51] Int. Cl.³ .............................................. B28D 5/00
[52] U.S. Cl. .................................... 125/30 R; 356/30; 51/165.72
[58] Field of Search .................. 356/30, 394, 399; 125/30 R; 51/165.72

[56] References Cited

U.S. PATENT DOCUMENTS 3,035,480  5/1962  Teucher ............................... 356/394

FOREIGN PATENT DOCUMENTS 7290 of 1976 South Africa .
2009642A 11/1978 United Kingdom .
2018173A 10/1979 United Kingdom .
2074480A 11/1981 United Kingdom .
2074910A 11/1981 United Kingdom .

Primary Examiner—Harold D. Whitehead
Attorney, Agent, or Firm—Shapiro & Shapiro

[57] ABSTRACT

A rough gem stone is centered by mounting the stone on a dop, providing an image of the stone, as seen normal to the axis, providing a reference shape which corresponds to the shape of a cut stone, and superimposing the stone image and the reference shape, altering the size of one relative to the other until the reference shape corresponds to the stone that can be cut from the rough stone, and altering the position of the rough stone until the stone image registers correctly with the reference shape. In a method of working the stone, the final radial dimension to which the stone is to be worked is estimated and is used for terminating working when the actual radial dimension reaches the corresponding value.

11 Claims, 2 Drawing Figures

CENTERING AND WORKING GEMSTONES

BACKGROUND OF THE INVENTION

Primarily, the present invention relates to centering a gem stone, e.g. so that a rough stone can be worked by a process which involves rotating the stone about an axis.

The working which is being primarily considered is bruting, which is the procedure of cutting or grinding a girdle on the rough stone, after the stone has been sawn (the sawn rough stone is called a "sawn-half"). However, the working could for instance be coning, which is forming a cone on the culet or table side of the sawn half.

Particularly referring to bruting, the present procedure in general is to brut, block at a culet half angle slightly greater than the desired angle to determine the position of the culet point, re-brut, and final block at the desired culet half angle. For a standard shape diamond, the first block would be at a 43° half angle and the second block at at 41° half angle.

In the art, the support which is used to support a gemstone while it is being worked is normally referred to as a "drop". In general terms, the support can have any suitable size or shape.

THE INVENTION

The present invention provides methods as set forth in claims 1, or 8, and a system as set forth in claim 9. The remaining claims set forth preferred features of the invention.

Primarily, the invention was devised for use with rough stones, e.g. sawn halves prior to bruting or even unsawn stones prior to sawing and bruting. However the invention can alternatively be used for quality control for examining stones which have been worked, e.g. bruted. In the case of bruting, the invention can be used to re-measure the bruted stone e.g to brut further or to determine the correct angles for polishing; in the case of a rough stone or a sawn half, the invention can indicate the largest possible bruted or polished, i.e. brilliant cut, stone of given proportions which can be fitted inside (this can be associated with centering for subsequent bruting or coning)—this can also take account of grain and of unwanted areas such as pique' (an inclusion within a stone). The invention can also indicate suitable "swindling", specially if reentrants or other defects are present—"swindling" is a term covering e.g. having the culet off centre, having the girdle out of round or tilting the girdle.

The proper measurement of the parameters in many cases depends upon there being no reentrant in the stone, and this can be determined manually or the presence of a reentrant can be automatically signalled in certain cases though in others (such as the presence of kinks in the crown), the system may be unable to detect reentrants fully automatically. However, once a reentrant, e.g. a hole, has been detected by say visual examination, the bottom can be sensed say with a stylus or fucussing arrangement, and the information so derived can be superimposed on other data furnished by the system. As a further possibility, the reentrant can be avoided by removing material around it, prior to examining the stone.

The stone should be rotated through at least 180°. The rotation may be discontinuous rotation, i.e. indexing or incremental rotation, or continuous (e.g. with strobed illumination). Though it is preferred to keep the viewer stationary and rotate the stone, it would be possible to keep the stone stationary and rotate the viewer around the stone—thus the rotation of the stone is referred to as "relative".

In a simple embodiment, the stone is moved radially, i.e. its position is altered until its image registers correctly with the reference shape. However, this is not essential. For instance, data can be furnished representative of the eccentricity of the stone and the stone can be centred later, e.g. by radial adjustment of the chuck of a bruting machine. Another possibility is to determine the correct axis, then move the dop automatically in the holder using such data.

The centering or aligning method of the invention can determine the position of the culet point and the position of the girdle on the rough stone, and gives a great advantage as it is possible in many cases to omit the first blocking referred to above.

In the reference shape, the ratio of the dimensions can remain the same, as the relative sizes alter, or one or more of the ratios can be altered, for instance to call up reference shapes for tall or shallow polished stones. Also, if suitable machines are available for working the stone, the parameters for working an out-of-round girdle can be provided. Thus in general, the invention can determine the largest polished stone of given proportions which can be fitted within a rough stone being examined.

In theory, it would be possible to alter the ratios of the image of the stone, but in practice it is found more acceptable to alter the ratios on the reference shape.

It would be possible to carry out the method without providing any real image or reference shape, performing the whole operation electronically without any screen and centering the stone (or providing the requisite data) automatically by a computer technique. However, in a simple embodiment, the stone image and the reference shape are superimposed, and the term "parameters of the reference shape" as used herein includes the pictorial representation of the shape e.g on a screen.

The reference shape itself may be defined by lines, which are called graticules herein, though the lines can be in any form desired, whether simple or complicated. The simplest form of graticule which is considered usable in practice is one having only vertical and horizontal lines, for instance horizontal lines at the culet point, the girdle and the table and vertical lines at the girdle edges and optionally on the centre line (the centre line is more useful for checking i.e. quality control, than for the initial setting). Alternatively however diagonal lines can be introduced to reproduce parts of the final shape, i.e. two diagonal lines to indicate the triangular culet outline with two vertical lines and a horizontal line to indicate the table. It will be appreciated that the terms "vertical" and "horizontal" are used merely for convenience, as though the stones were resting with its culet point uppermost.

The reference shape can be generated in any suitable way, a simple way being that of using a half-silvered mirror and an image, another way being that of using two television cameras, one of which views a reference shape, and a preferred way being that of generating the reference shape electronically.

DESCRIPTION OF PREFERRED EMBODIMENTS

Figure 1:
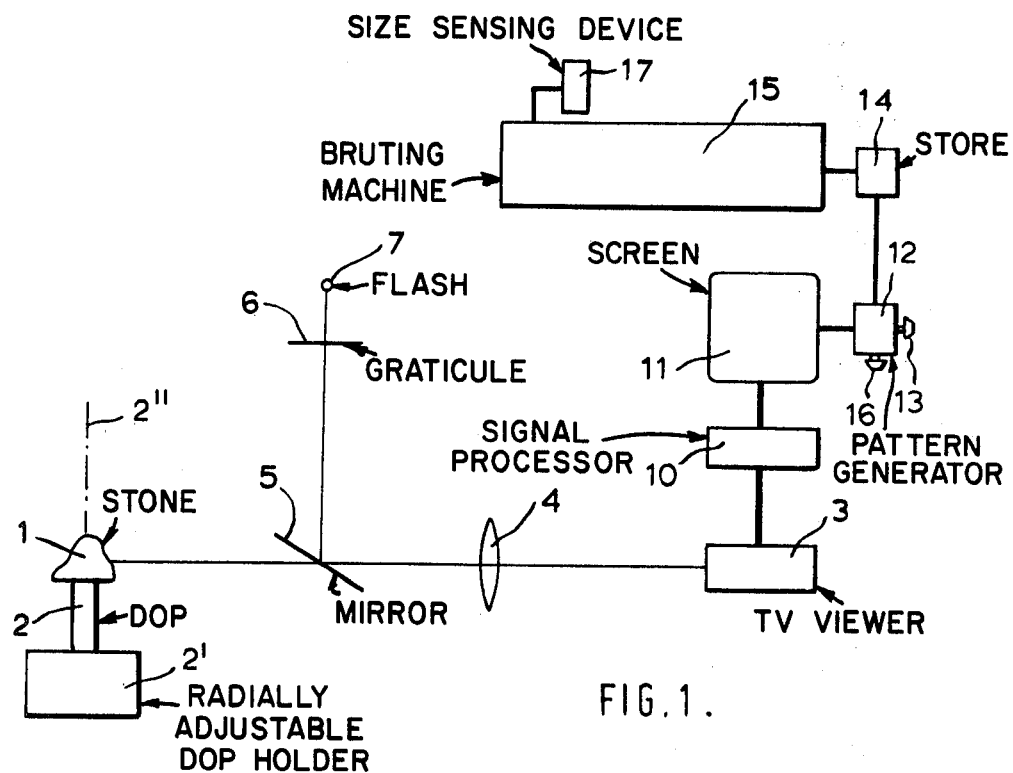
Figure 2:
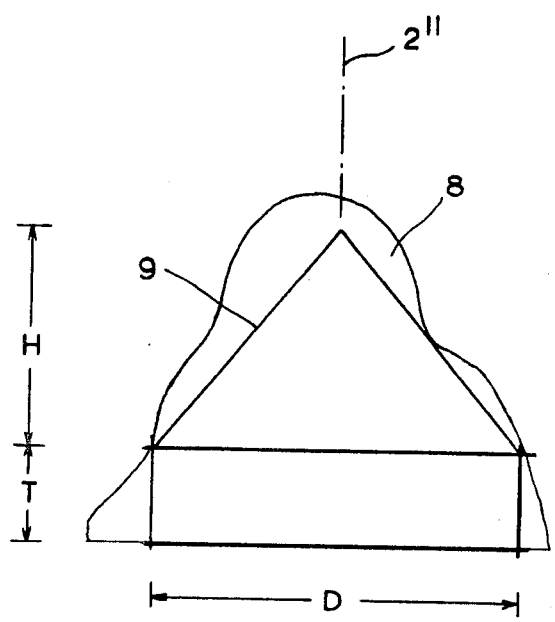

The invention will be further described, by way of example, with reference to the accompanying drawing, in which:

FIG. 1 is a schematic side view of a simple system in accordance with the invention; and FIG. 2 is a view of a TV screen used in a system in accordance with the invention.

FIG. 1 in essence shows a rough diamond 1 stuck to a dop 2 and viewed by a TV viewer 3 through a lens system 4. There is also a slightly "slivered" mirror 5, a graticule 6 and a flash 7, but these will be referred to later. Though the axis of viewing is shown intersecting the middle of the diamond 1, it is not very critical and could for instance intersect the expected girdle or the table (top of the dop 2). The axis of viewing is conveniently strictly at 90° to the axis 2" of the dop 2, but need not be so provided it is roughly so, so that the image within the viewer 3 or on the screen is as seen normal to the axis of the dop 2. The axis of viewing need not intersect the axis 2" of the dop 2. Associated with the TV viewer, there is a screen on which is projected an image of the diamond 1, as seen normal to the axis, and also a superimposed reference shape or graticule which corresponds to the shape of a cut stone and which is centered in effect on the notional axis of working (in effect, the reference shape represents its own parameters). As explained hereafter, the size of the graticule, though temporarily fixed, can be altered manually, thereby altering its size relative to the image of the diamond 1. The image of the diamond 1 on the screen can be enhanced optically or electronically to give a well-defined edge. For instance, the image can be video-sliced and the edges only detected or sensed. The best discrimination is obtained with the stone 1 dark against a light field (a silhouette), looking at the rise time of the edge of the image and triggering at the correct point, e.g. at the point where the intensity is 75% of that of the field. Controls can be provided for defining the area on the screen which is occupied by the image of the diamond 1.

In a suitable procedure for centering the diamond 1, the dop holder 2' described in British patent specification No. 2,009,642A is used to hold the dop 2 and alter its position radially, the holder axis nominally being coincident with the notional axis of working and the dop axis remaining parallel to the holder axis.

It is found possible to provide the operator with a simple lever or knob control for altering the size of the graticule, and a simple procedure can be as follows:

(a) Roughly correct graticule size;
(b) Center the diamond 1;
(c) Finally correct the size of the graticule;
(d) Rotate the diamond through 90°;
(e) Center the diamond 1;
(f) Correct the size of the graticule, if it is too large;
(g) Rotate the diamond 1 continuously through 180° to ensure that no parts on the outline of its image would be within the shape of the polished diamond indicated by the graticule.

This is illustrated in FIG. 2, which shows the image 8 of the diamond 1 and a graticule 9 which reproduces the triangular shape of the culet and indicates the table by a rectangular shape, the upper line of the rectangle and the two verticals indicating where the bruted girdle will be.

Referring to the dimensions indicated in FIG. 2, the T:D ratio can be varied or the T:D and H:D ratios can be varied. The variation will be under control of the operator and may be continuous though stepped variation (say six to eight steps over the possible range) is simpler. In the simplest form, a programmed memory chip can be changed. This variation enables one to obtain the maximum yield, i.e. the heaviest stone possible, from a rough stone.

The use of the diagonal lines indicated in FIG. 2 is highly beneficial in that, when the operator rotates the diamond 1, it can be determined if all of the diamond 1 is outside the indicated final shape, and the final shape can be either increased or decreased in size. By scanning the TV picture and producing information comparing the picture and the graticule, the system can be arranged to flag any edges of the diamond image which project outside or fall inside the graticule.

Though not indicated, there can be a centre vertical line in the graticule with an operator-controlled switch for showing it.

Once the position of the diamond 1 has been correctly determined, it is locked. It is then possible to read a code around the holder and store the information to be called up by the bruting machine when the holder is put in the bruting machine to indicate the serial number of the holder. In addition to this, readings can be automatically taken off the screen or electronically before the diamond 1 is removed. Thus the holder serial number and the graticule dimension (plus any ratio change) is put in a store, and further information can be inserted in the store including the maximum radius of the diamond 1 measured when the diamond 1 was rotated (corresponding to the point at which bruting should start) and the height of the diamond 1 at different radii so that the bruting machine can adjust its stroke length to the minimum required to brut the stone, thus maximising the speed of bruting.

When the holder has been mounted in the bruting machine, the machine calls up the stored information. The machine can feed in fast until the stone is just touching the bruting tool (which may be another stone whose radius is already stored in the machine), the stroke length can be adjusted and the condition set at which the machine will automatically stop when the final diamond size is reached. The machine can be arranged to automatically reduce the rate of feed before the final size is reached, to allow a smooth or polished girdle to be produced.

The radius of the stone while in the bruting machine can be measured by an optical system using linear photodiode arrays, a TV system or a mechanically tracking servo system. Suitable systems are disclosed in G.B. Nos. 2,074,480A and 2,074,910A. The measurement can be made when the stones are in contact and when out of contact, to allow for spring in the dop, holder and bearings etc. The deflection of the dop can be used if required, as a measure of the bruting force, and allowed to adjust the bruting machine's feed rate to keep the force constant or to slow the feed if the maximum force allowable is approached.

The diamonds or stones can be stuck onto the drops with their table side down, though as an alternative the culet can be down.

For stones of regular shape, i.e. near the traditional shape for that stone, the centering system could automatically center the stone as a result of processing the signals from the video system and thus moving the stone to make the distance from the stone centre to each of the corners as equal as possible. A sub-routine could be introduced so that if the ratio between maximum and minimum dimension exceeds a predetermined amount when the stone has been centered automatically, the stone would be rejected for further manual centering.

As an alternative, the centering system could use a light optical projector with for instance one or more diode arrays to sense the position of the stone, e.g. on the TV screen.

As a further variation, it would be possible to use a zoom lens and a graticule of fixed size and a second TV viewer for producing the graticule image.

In a further modification indicated in FIG. 1, the mirror 5 allows the image of the graticule 6 to be projected onto the TV viewer 3 in a period between examining stones, i.e. while the stones are being changed. The flash 7 illuminates the graticule 6 and the TV system then reads the position of the graticule lines and uses these to generate and store correction signals in the memory of a processor so that the dimensions read out to store would be absolute and would not be influenced by non-linearity of the TV system and defects of the lens system. It is normally considered that in TV systems, it is very expensive to produce linearity better than 1%.

As an alternative to using a machine readable number on the holder, a small (bar code) label could be printed at the end of the centering procedure, the label then being manually or automatically stuck round the stone, dop or holder. The label code would be machine readable and a new label would be used each time a new stone was positioned in the holder.

The TV viewer 3 can be connected to any suitable equipment, and such equipment is known. FIG. 1 shows schematically the TV viewer 3 connected to an electronic unit 10 for processing and enhancing the image, screen 11 on which are projected the image of the diamond 1 and the image of the graticule 6, a generator 12 for generating the reference shape or graticule 9, a manual knob 13 for altering the size of the graticule 9, and a store 14 for storing the maximum radius and heights of the diamond 1 at different heights and then acting as input means to feed the data into a bruting machine 15 such as that disclosed in GB No. 2,018,173 A. The store 14 can be purely electronic or could just be a machine readable number or label as described above. If the diamond 1 is to be centered on the machine 15, the store 14 would also hold data representative of the eccentricity of the diamond 1 and centering would be performed by manual adjustment of a further knob 16 followed by automatic adjustment when the diamond 1 is mounted in the machine 15. The size or diameter of the diamond as it is being bruted is sensed by a device 17 which automatically stops the machine 15 and terminates working when the size or diameter of the diamond corresponds to that previously determined—as indicated above, the device 17 can be as described in GB No. 2,074,480A.

If the comparison procedure is being carried out electronically, the screen 11 and knobs 13, 16 are not required, but the generator 12 would have to have suitable computing capacity. The computer (12) can be programmed in any convenient manner. However one suitable algorithm is:

(a) Read outline data of image as viewed from one angle, by sensing the edge on each line scan—these can be say 300–1000 lines, depending on the resolution required;

(b) Choose a location for the vertical axis through the culet of the diamond 1 by specifying the coordinates of the intersection of the axis with the plane of the table of the diamond 1;

(c) Locate the position of this axis in the image view being examined;

(d) Find the size of the largest reference shape (template) 9 centered on the axis of (b) that fits inside the image view; remember this size;

(e) Have all possible culet positions been examined for this imge view?—if no, return to (b)—if yes, pass on to (f);

(f) Read outline data of image as viewed from next angle, repeating (a) to (e) for this new image;

(g) Re-examine culet axis location and if necessary shrink the reference shape 9 already determined until it fits the new image; remember this size;

(h) Have the images been examined as viewed from all angles?—if no, return to (f)—if yes, pass on to (i);

(i) This determines which culet position admits the largest reference shape 9 that fits all the images; remember its size and the coordinates of the corresponding axis.

A cut stone can be examined using the manual procedure outlined above, a purely visual examination being made of the image on the screen 11 once the stone has been centered and the graticule 9 correctly sized.

We claim:

1. A method of centering a rough gem stone so that the stone can be worked by a process which involves rotating the stone about an axis on which the stone has been centered, the method comprising:

providing an image of said stone, as seen generally normal to an axis through said stone;

comparing said image with the parameters of a reference shape which corresponds to the shape of a stone that can be cut from said rough stone, said image and said reference shape being of fixed but alterable relative sizes;

altering the relative sizes of said image and said reference shape until the reference shape parameters correspond to the stone that can be cut from said rough stone;

providing at least one further image of said stone with said rough stone in a different relative angular position about said axis;

comparing said further image with said parameters;

if said reference shape is too large, reducing the size of the said reference shape; and using indications derived from said altering to center said rough stone.

2. The method of claim 1, and further comprising radially altering the position of said rough stone until said image registers correctly with said reference shape.

3. The method of claim 1, and further comprising furnishing data representative of the eccentricity of said rough stone, and centering said rough stone using such data.

4. The method of claim 1, wherein said image and said reference shape are superimposed.

5. The method of claim 1, wherein said image is compared electronically with said reference shape without provision of a visible reference shape.

6. The method of claim 1, and further comprising providing data indicating the size of said cut stone as determined by said altering mounting said rough stone in a machine for working said rough stone by a process which involves rotating said rough stone about an axis, feeding said data to said working machine, sensing the size of said stone as it is being worked, and terminating working when the size of the stone corresponds to that previously determined.

7. The method of claim 1, wherein the ratio of at least one dimension of said reference shape to another is altered, whereby higher or shallower cut stones can be produced.

8. A method of examining a cut gem stone for quality control, said stone having an axis of symmetry, comprising:

providing an image of said stone, as seen generally normal to said axis;

comparing said image with the parameters of a reference shape which correspond to the shape of a correctly cut stone, said image and said reference shape being of fixed but alterable relative sizes;

altering the relative sizes of said image and of said reference shape until the reference shape parameters correspond to a correctly cut stone which is nearly as possible the same size as the stone being examined;

providing at least one further image of said stone with said stone being examined in a different relative angular position about said axis;

comparing said further image with said parameters;

if said reference shape is too large, reducing the size of said reference shape; and radially altering the position of said stone being examined until said image registers correctly with said reference shape.

9. A system for centering a rough gem stone so that said rough stone can be worked by a process which involves rotating said rough stone about an axis, the system comprising;

means for holding a support for said rough stone;

means for providing respective at least temporarily fixed-size images of said rough stone when supported on said support, as seen generally normal to an axis through said rough stone, at a number of different relative angular positions of said stone about said axis;

means for providing parameters of an at least temporarily fixed-size reference shape which corresponds to the shape of a stone that can be cut from said rough stone;

means for comparing said image and said parameters;

means for altering the relative sizes of respective said images and of said reference shape until said parameters correspond to said stone that can be cut from said rough stone, whereby the size of the cut stone can be determined; and means for moving said rough stone radially in order to center it.

10. The system of claim 9, and further comprising means for providing data indicating the size of the cut stone as determined by finding the size of said image relative to said reference shape, a machine for working said rough stone by a process which involves rotating said rough stone about the axis on which said rough stone has been centered, input means for feeding in said data into said machine, means for sensing the size of said stone as it is being worked, and means for terminating working when the size of the stone being worked corresponds to that previously determined.

11. The system of claim 10, as further comprising means for altering the ratio of at least one dimension of said reference shape to another dimension thereof.

* * * * *